United States Patent [19]
Fenn

[11] Patent Number: 5,669,377
[45] Date of Patent: Sep. 23, 1997

[54] NASAL BAND AND METHOD FOR IMPROVED BREATHING

[76] Inventor: Arthur C. Fenn, 5 Parkside Way, Greenbrae, Calif. 94904

[21] Appl. No.: 752,603

[22] Filed: Nov. 19, 1996

Related U.S. Application Data

[63] Continuation-in-part of Ser. No. 675,356, Jul. 5, 1996.
[51] Int. Cl.$^6$ .............. A61F 5/08; A61M 29/00; A61M 15/08; A62B 7/00
[52] U.S. Cl. .............. 128/200.24; 606/199; 606/204.45
[58] Field of Search .............. 128/200.24, 207.18, 128/898; 602/902, 54, 58, 5, 6, 12, 14, 16, 17, 46, 47, 61, 74; 606/199, 204.25, 204.45, 191, 196, 198

[56] References Cited

U.S. PATENT DOCUMENTS

| | | |
|---|---|---|
| 5,476,091 | 12/1995 | Johnson . |
| 5,533,503 | 7/1996 | Doubek et al. . |
| 5,546,929 | 8/1996 | Muchin . |

*Primary Examiner*—Vincent Millin
*Assistant Examiner*—Robert N. Wieland
*Attorney, Agent, or Firm*—Thomas W. Tolpin

[57] ABSTRACT

A user friendly nasal band and method are provided which lifts up the tip of the nose, enlarges the nostrils and shortens the effective length of the nasal passageways. The light weight nasal band provides a comfortable sleep band and dilator strip which improves sleep and makes breathing easier for many patients. Advantageously, the sleep band and method also reduces or eliminates snoring for many patients. This is accomplished by improving the nasal airway. An improved nasal airway minimizes mouth breathing which prevents vibration of the palate, tongue, and pharyngeal walls thus reducing the noise of snoring. Air passing through the mouth during sleep causes vibration of the relaxed tongue, palate, and pharyngeal wall resulting in the noise of snoring. The nasal band also provides an attractive sports band which minimizes collapse of the nasal sidewalls during jogging or other strenuous exercise so that athletes can continue to breathe through their nose rather than breather through their open mouth. The nasal band is preferably worn vertically and stretches along the bridge of the nose from the tip of the nose to the upper part of the nasal bridge or forehead. The nasal band can comprise a waterproof adhesive tape with a lower tip portion, a bridge portion, and a top portion.

20 Claims, 1 Drawing Sheet

NASAL BAND AND METHOD FOR IMPROVED BREATHING

RELATED APPLICATION

This application is a continuation-in-part of the application of Arthur C. Fenn, Ser. No. 08/675,356, filed Jul. 5, 1996, for a Nasal Tip-Lift Adhesive Band for Improved Breathing.

BACKGROUND OF THE INVENTION

This invention pertains to nose devices and, more particularly, to a nasal band and method for improved breathing and reduced snoring.

Many people have difficulty breathing through their nose. Some causes for restricted breathing are congestion of the nasal lining from allergies, deviation of the nasal septum, i.e., the partition between the two nostrils, which narrows one or both nasal chambers, or by a droopy nasal tip.

When people exercise, nasal breathing becomes more difficult and people are forced to open their mouths to get enough air. When exercising, it is necessary to breath rapidly. Upon rapid breathing, a negative pressure is created in the nasal chamber forcing the lower sides of the nose to collapse which obstructs breathing. If nasal breathing becomes obstructed, it is necessary to breath through the mouth in order to obtain an adequate amount of air. When a person becomes a mouth breather, the important functions of the nose are bypassed.

The nose performs the following functions; air humidification, air filtering, and warming of the air; all these functions are preparing the air for its entrance into the lungs. The nose detects any noxious fumes in the air and is also the initial contact of any air-borne allergens. The nose accounts for approximately half of the total airway resistance to airflow. Nasal obstruction can contribute to an increase in snoring and sleep apnea frequency and severity. Snoring sounds have been associated with increased upper airway occlusion. Upper airway narrowing, collapsibility and resistance are recognized factors contributing to snoring and obstructive sleep apnea. Certain loud snorers have an increased internal resistive load that results in repetitive arousals from sleep.

Sleep apnea and snoring are common conditions that affect about 5–10% of the adult male population in the United States. Snoring refers to just the noise while sleep apnea is a medical condition in which a person actually stops breathing for periods of time while sleeping. Snoring by itself is much more common and affects approximately 50% of the males and 30% of females. Snoring probably can be considered the pre-clinical state for the development of obstructive sleep apnea syndrome (OSAS), which is characterized by repetitive episodes of apnea during sleep accompanied by signs and symptoms of hypoxic stress and sleep interruption. Those patients complain of tiredness, excessive daytime somnolence, headaches, and poor job performance. This problem may cause marital difficulties and may very well contribute to separation and divorce. Patients affected by this condition frequently have serious morbidity such as arterial hypertension, angina, myocardial infarction and stroke, dementia in the elderly age groups, automobile accidents resulting in severe trauma or even death.

Obstructive sleep apnea afflicts about 2 to 5 million Americans and causes snoring and excessive daytime sleepiness, as well as other cardiovascular, pulmonary, and behavioral problems. Inspiratory nasal flow in apneic patients can be 30% less than in individuals with normal sleep patterns. Various surgical procedures can be used to improve the functional patency of the airway, but while successes are frequent, they are not uniformly predictable. Furthermore some patients may not be acceptable candidates for surgery.

Snoring and apnea are associated with instability, vibration, and collapse of the valve situated at the pharyngeal level. In the upright and awake state, the negative pressure created in the thorax will move the air in. Stability is present because the muscular tone stiffens the walls. During sleep the muscular tone is diminished. Snoring and apnea occur more frequently in people with smaller noses, higher pharyngeal resistance, smaller pharynxes, or lower hyoid bones with longer pharynxes, and in persons with diffused crowding of the soft tissue inside the valve. The airflow needs to move faster inside a smaller tube and the negative pressure builds up. All these factors can combine with one another to create instability and pharyngeal collapse. Furthermore, obstruction and apnea can effect muscle tone. Sleep or the presence of alcohol in the blood decreases or even paralyzes hyoid muscle tone. Moreover, in severe apnea and snoring, the hyoid bone has a tendency to move lower. The tongue is displaced backward within the posterior airway space.

There are three key factors to explain snoring: The first is sleep, with its muscular relaxation. The second is inspiratory negative pressure, through which air is dram in through the nose and pharynx. The third one is the pharynx, the muscular collapsible part of the upper airway. Mild snorers are less troubled when they sleep on their sides or in the prone position. Unfortunately, almost all obstructive sleep apnea patients experience airway problems in all positions of sleep. Many snorers and apneic people have an inferior turbinate hypertrophy. Anterior rhinomanometry also can have an increased nasal resistance. Maximal nasal resistance is usually located at the nasal valve area, which compromises the anterior part of the inferior turbinate. Most snorers have an abnormal tendency to nocturnal collapse of the upper airway. There is also a direct relationship between the tendency to snore and the degree of negative pressure needed to initiate pharyngeal collapse. Snoring is secondary to abnormal vibrations and collapse of the pharyngeal part of the upper airway.

The inspiratory drive expands the thorax, creating a negative inspiratory pressure, that brings air into the body. At the same time, negative pressure is manifest in the only collapsible part of the upper airway, the pharynx. This area behaves like a valve in which two rigid tubes are united by a collapsible tube. This pharyngeal valve, with its mobile walls, and the tongue can both collapse when the negative inspiratory pressure outbalances the tissular resistance to collapse.

During the day, the muscular tone of the pharynx equilibrates negative pressure and the pharynx is kept open. At night, the muscular tone is diminished, so that the pharyngeal valve is more flaccid. The thorax, however, continues building up negative pressure and the tendency toward collapse is present.

The nose is a structure that protrudes from the anterior portion of the skull and serves as a passageway for air to and from the lungs. The nose filters the air, warming, moistening, and monitoring the air for impurities that might irritate the mucous lining of the respiratory tract. The nose also serves as the organ of smell and assists in speech. The nose has an internal portion and an external portion. The external portion, protrudes from the face and is considerably smaller than the internal portion, which is positioned over the roof of the mouth. The hollow interior portion of the nose is separated into a right cavity and a left cavity by a septum. Each cavity is divided into the superior, middle, and inferior meati by the projection of nasal conchae. The external portion of the nose is perforated by two nostrils and the internal portion by two posterior nares. The pairs of sinuses that drain into the nose are the frontal, maxillary, ethmoidal, and sphenoidal sinuses. The ciliated mucous membrane lines the nose, closely adhering to the periosteum. The mucous membrane is continuous with the skin through the nares and with the mucous membrane of the nasal part of the pharynx through the choanae. The mucous membrane contains the olfactory cells which connect with the olfactory nerves.

The nose has the important function of first contact with inspired air. This air is laden with pollutants, suspended material, microbes, and noxious substances. Air can be dry and cold and often needs warming and humidification before entering the lower respiratory tract. The nose also serves as a sensitive detector of air-borne chemicals and helps sense flavor of ingesta. The nose further serves an important role in the immune system because it is the first site of contact of many air-borne allergens with the body's defense system.

The nasal chamber is divided into the vestibule and passages. The vestibule is a skin-lined anterior segment that gives rise to the vibrissae, or nasal hairs. The skin yields to respiratory epithelium at the limen vestibuli (os internum), which is also the location of the nasal valve area. The narrowest portion of the nasal cavity is at this level. The nasal valve area encompasses the junction of the ala with the pyriform aperture, the caudal end of the upper lateral cartilages, the floor of the nose, and the head of the inferior turbinate. The nasal passages are quite narrow and usually range from 1 to 2 mm between the free edges of the turbinates and the septum. The nasal passages also have a convoluted shape. The turbinates are usually 5 to 8 cm in length. The nasal cavities open on the face through the pear-shaped anterior nasal aperture and communicate with the pharynx. Each cavity is narrower at the top than at the bottom.

The nasal fossa, are approximately equal chambers of the nasal cavity, that are separated by the nasal septum. The nasal fossa open externally through the nostrils and internally into the nasopharynx through the choanae. Each fossa is divided into an olfacotry region comprising the superior nasal concha and part of the septum, and a respiratory region, providing the remainder of the chamber. Overhanging the three meatae of each fossa on the lateral wall are the corresponding superior, middle, and inferior nasal conchae. The superior meatus extends obliquely about half way along the superior border of the middle concha. The middle meatus continues into the atrium and bulges on the lateral wall at the bulla ethmoidalis. The inferior meatus courses below and lateral to the inferior nasal concha and contains the opening of the nasolacrimal duct. The olfactory region is located in the superior part of the fossa and contains olfactory cells, olfactory nerves, and olfactory hairs. The respiratory region is lined with mucous membrane, numerous glands, nerves, a plexus of dilated veins, and blood spaces. The plexus can be easily irritated causing the membrane to swell, which block the meatae as well as the sinus.

The nasal mucosa is innervated by branches of the ophthalmic and maxillary divisions of the trigeminal nerve. The anterior portion of the nose is innervated by branches of the anterior and posterior ethmoid nerves and twigs off of the nasociliary division of the ophthalmic nerve. The posterior portion of the nose is innervated by branches of the maxillary nerve. The lateral posterior superior nasal nerve emerges from the sphenopalatine foramen to innervate the posterior ends of the inferior and middle turbinates. The medial posterior superior nerve arches over the posterior portion of nasal vault to innervate the posterior nasal septum. The posterior lateral nasal nerve innervates the posterior floor of the nose and is a branch of the palatine nerves originating from the maxillary nerve.

The nasal mucosal surface is a pseudostratified ciliated columnar epithelium that begins posterior to the nares. The nasal mucosal surface is covered with a mucoid blanket that is of serous consistency around the cilia but more mucoid on the surface. The predominant cell is a ciliated cell. The mucous blanket allows breathing of the cilia to occur in the low viscosity lower segment. The upper layer is transported by the whipping motion of the tips of the cilia. Each of these cells has cilia and additional microvilli on the apical surfaces.

The lamina propria of the nasal cavity contains stromal cells, inflammatory cells, nerves, and blood vessels. Mast cells, basophils, and other leukocytes allow rapid release of inflammatory mediators upon detection of microbiologic and chemical invasion. A brisk inflammatory response is possible in the nasal mucosa. Within the submucosa are compound alveolar glands containing cells whose cytoplasm is distended with acid mucopolysaccharide. Plasma cells surround these glands. Lymphoid nodules are also found in the submucosa.

Numerous blood vessels pass course through the submucosa. The arterioles are quite deep and supply periglandular and subepithelial capillaries. The afferent capillaries empty into large venous sinusoids, the walls of which are surrounded by abundant elastic tissue and smooth muscle. The sinusoids drain into a deeper venous plexus. Arteriovenous anastomoses allow rapid engorgement of the sinusoids. Dilation of the sinusoids can occur if there is arteriolar dilation or constriction of the deep veins.

The blood supply follows an anterior and posterior pattern. The anterior portion of the nose is supplied by the anterior and posterior ethmoid arteries, branches of the ophthalmic artery, which in turn derives from the internal carotid artery. The posterior portion of the nose is supplied by the sphenopalatine artery, a branch of the internal maxillary artery that originates from the external carotid system. There is extensive collateral flow between these two vessel systems and the contralateral side.

The principal mechanisms of protection provided by the nose are attributable to the presence of a layer of mucus on its lining surface. Most of the posterior two-thirds of the nasal cavity is lined by pseudostratified ciliated columnar epithelium, which contains goblet cells and includes a lamina propria housing both mucous and serous glands. Anteriorly the vestibule is lined by keratinizing stratified squamous epithelium. Behind this a transition occurs from keratinizing to nonkeratinizing squamous epithelium. Further posteriorly, the epithelium becomes flatter and changes to the pseudostratified ciliated columnar epithelium that covers the bulk of the internal portions of the nose. On the exposed surfaces of the turbinates and over the crest of septal, is the mucosa which becomes flattened or even squamous as it is at the margins of septal perforations. This feature seems to be related to the turbulence of the air flow. Above the superior turbinates, the nasal surface is covered by olfactory epithelium.

The size and shape of the nares play an important role in nasal air flow and resistance. When most of the air passes through the nose, it bypasses the tongue and palate thereby reducing vibration of the tongue and palate. The shape of the nares can be altered by both dilating and constricting voluntary muscles. The nares are often narrowed in cosmetic rhinoplasty, occasionally resulting in marked diminution in nasal air flow. The nasal ala obtains some rigidity from the upper and lower lateral cartilages. On inspiration, a decrease in pressure occurs in the nose, tending to collapse the semirigid vestibular wall. The cranial end of the vestibular wall is sometimes referred to as a valve. As the valve closes and air flow decreases, the pressure upstream rises, tending to open the valve and thereby acting as a regulatory mechanism for air flow. The pressure required to close the valve can be altered by removal of upper and lower lateral cartilage, making the vestibular wall less rigid, and also by minor deviations of the caudal end of the nasal septum. The septal deviations, by narrowing the vestibular opening, cause a further lowering of transmural pressure.

Resistance to nasal airflow is an important aspect of nasal function. It generates the turbulent flow that allows interaction between the airstream and the nasal mucous membrane surface. There is a cyclic change of nasal airflow resistance every 3 to 4 hours that is known as the nasal cycle. On each side of the nose, there is alternate constriction and dilation of the nasal mucosa in such a way that the overall resistance remains unchanged. When an individual lies on a side, the underlying nasal cavity tends to become congested, thereby giving rise to stimuli that cause the patient to roll over and more equally ventilate both lungs.

Nasal airflow resistance forms approximately one half of the resistance of the entire respiratory tract. The main site of nasal resistance is the nasal valve, which is the flow-limiting segment. There is a wide range of nasal airflow resistance, which tends to increase with recumbency and cold inspired air. When carbon dioxide levels are increased, nasal resistance is decreased. With extremes of inspiratory effort, there is collapse of the nasal valve because of elevation of the transmural pressure of the nose. This occurs in mesorrhine or leptorrhine anatomic types. The platyrrhine type is not subject to collapse in this way. There are advantages in a cold, dry environment for this mechanism. Fluttering of the ala with rapid inspiration will tend to increase the interaction of the air stream with the warm, most mucosal surface, resulting in better nasal air conditioning. The dilator alae muscle also prevents collapse during deep inspiration.

The open free feeling of nasal breathing depends in large part on nasal airflow resistance. The sensation of nasal obstruction is very complex. Nasal resistance should be within certain limits for a person to feel that breathing is normal. If the nasal resistance is too high or too low, there is a sense of nasal obstruction. Nasal resistance also affects patients with atrophic rhinitis for which nasal obstruction is the most common complaint. Furthermore, maintenance of airway resistance during nasal breathing assists in preventing alveolar collapse during expiration. A certain range of nasal resistance appears to be preferred for maintenance of comfort and health. Sometimes, nasal surgery has to be performed to improve the nasal airway flow.

There are many factors that influence nasal resistance and affect the state of engorgement of the nasal mucosa. For example, gravity affects venous engorgement. Patients with unilateral nasal obstruction avoid sleeping on the patent side. Exercise and emotional states that impact the autonomic nervous system affect nasal resistance as well. The decrease in nasal resistance after exercise results from local release of norepinephrine by sympathetic nerve endings which cause stimulation of alpha receptor sites.

Pharyngeal resistance to airflow is normal. This phenomenon always occurs more often in the male. In a recumbent, healthy subject, this resistance builds up caused by loss of muscular tone. This is accentuated by the backward gravitational movement of the mobile part of the pharynx. In cases of severe apnea, resistance inside the cavum, pharynx, and supraglottic region increases, as well as the negative pressure for air intake.

Inflamation is a common cause of nasal obstruction. Rhinitis may be due to infection (viral, pyogenic bacterial, mycobacterial) irritants, pollutants, topical medications or inhaled drugs.. Other inflammatory processes, such as sarcoidosis, Sjögrens syndrome, Wegener's granulomatosis, and necrotizing sialometaplasia, can also cause rhinitis. Antiadrenergic agents, such as reserpine, may lead to vascular engorgement. Inflammatory nasal polyps, pyogenic granulomas, and adenoid hypertrophy may be the end result of any number of microbiologic or chemical insults or neurovascular imbalances (vasomotor rhinitis). Rare infections (aspergillosis, atypical mycobacterial) may be associated with the acquired immune deficiency syndrome (AIDS). During upper respiratory tract infections, pulmonary impairment may occur in otherwise normal children. Respiratory infections can precipitate an asthmatic attack. There is a transitory bronchodilation or bronchoconstriction for various stimuli in the nose.

A spontaneous congestion-decongestion reflex is a reciprocal change in which congestion on one side is accompanied by decongestion on the other side so that the total resistance remains relatively constant. This reflex provides a normal nasal cycle which can repeat every three hours or so. The reflex appears to be central rather than peripheral, since topical administration of epinephrine prevented engorgement but did not influence the cycle itself.

During normal speech there are times when the nasal cavity communicates with the oral cavity and times when it does not. It does not play a role in the production or alteration of vowel sounds but acts as an additional resonating chamber when certain consonants are uttered. During phonation of the nasal consonants /m/, /n/, and /ng/, as in music, naris and ring, the velopharyngeal port is open and the sound produced is emitted through the nose rather than the mouth. If the nose or nasopharynx is obstructed, denasal speech or rhinolalia clausa may result, depending upon the degree of obstruction. If the obstruction is severe, there is substitution of /b/ for /m/, /d/ for /n/, and /g/ for /ng/.

Nasal airflow can be divided into two categories, depending on the quantities being studied. The first category pertains to nasal airflow resistance and involves the measurement and calculation of air volume flow rate and its relation to drop in pressure along the nasal airway. As such, air is treated as a homogeneous fluid whose flow is driven by the drop in pressure. The second category is more complicated and involves the exchange of a particular molecular species or heat between the air stream and the walls of the nasal cavity, such as the humidification and warming of inspired air accompanied by the evaporation of water vapor from the nasal mucosa. It is customary in fluid mechanics to refer to the first category as bulk flow or momentum transport and to the second category as mass and heat transfer.

Important aspects of airflow through the nose is affected by:

1. A narrow constriction just beyond the nasal entrance (nasal valve).

2. A bend at or just beyond the nasal entrance constriction.

3. A large cross-sectional area of narrow width along the main nasal passage.

4. A passageway between the nasal cavity and paranasal sinuses.

5. A bend and slight constriction at the junction of the nose and nasopharynx.

6. The presence of adenoid tissue lining the posterior nasopharynx which serves to allow contact between particulate matter and the immune system.

Air enters the anterior nares at an angle of inclination, such as approximately 60 degrees from the horizontal. At about 1.5 to 2.5 cm from the opening is the nasal valve. At this point, the air stream bends horizontally. Most of the air flow, through the nose is adjacent to the middle meatus which can be at about 1 mm from the surface. The air stream eventually bends inferiorly in the nose at the nasopharynx. During expiration, most of the air penetrates uniformly through the entire nasal passageway. The os internum, or nasal valve area has an area of approximately 0.32 cm$^2$ per side. The airflow at this point can be at a flow rate, such as 12.5 L per minute or at 6.5 m per second, and is the fastest velocity in the entire airway. Once the air passes the os internum, the cross-sectional area greatly increases and the velocity falls rapidly. The sudden large decrease in velocity along with viscous retardation of air by the large surface area often gives rise to turbulent nasal flow.

The major flow passes through the middle meatus above the inferior turbinate. A small amount of air flows along the nasal floor. An even lesser amount of air flow passes upwardly and forms a standing eddy at the upper portion of the nasal chamber in the olfactory area. This increases with sniffing. Within the nasal cavity itself, the velocity of airflow can be 2 to 3 m per second. In the nasopharynx, the velocity can increase to 4 m per second. There is very little pressure change in the air beyond the nasal valve.

During inspiration an inadequate nasal airway creates an excessive negative pressure in the collapsible pharyngeal airway, which aggravates nasal obstruction. Improvement in the nasal airway such as allergy management and nasal surgery can help some snorers and a few apneic patients.

The fluid mechanics equations of motion for air flow in the nasal cavity is dependent upon the Reynolds number ($N_{re}=\bar{u}d/v$) and the frequency parameter ($a=d\sqrt{w/v}$), where $\bar{u}$ is the average airflow velocity in the external nares, w is the angular frequency of breathing (equal to 2 f, where f is the breathing frequency in breaths per second), d is the diameter of the external nares, and v is the kinematic viscosity of air.

Nasal airlfow can also be described mathematically by the use of Poiseuille's law $$V = \frac{\Delta P \pi r^4}{8\eta l}$$

where v is nasal airflow rate, r is radius of the conduit, η is coefficient of viscosity, 1 is length of the conduit, and ΔP is the drop-in pressure. The relationship applies only to laminar airflow.

There is a tendency for turbulent air flow in human noses. Under conditions of quiet breathing air flow can be laminar. Any decrease in cross sectional area or increase in respiratory rate may cause turbulent flow.

One of the simplest of these techniques for measuring nasal resistance is the introduction of two tubes into the pharynx through the mouth. Air is injected at a predetermined rate through one tube. The patient should close the glottis so that air emerged through the nose. The pharyngeal pressure, together with the constant and predetermined flow rate, can be used to determine nasal resistance. The nonlinearity caused by turbulence can be controlled by plotting pressure flow measurements at different resistances.

Anterior and posterior rhinoscopy may detect mechanical obstructions either due to deviation of the nasal septum, hypertrophy of turbinates, polypoid mucosa, polyps, neoplasm, etc. Often the soft plate is elongated and the uvula is much larger than normal. The tongue may be large and the oropharyngeal airway may be reduced due to redundant soft tissue. Pharyngoscope and indirect laryngoscopy can be done either with the use of laryngeal mirror or flexible fiber optic nasopharyngeal laryngoscope.

The sleep study of polysomnography measures sleep: actual measurements include electroencephalography (EEG), eye movement recording, electrocardiogram (ECG), electromyography (EMG), respiratory effort, respiratory flow (oral, nasal, or combination of both), and oxygen saturation. These studies can be useful to define the sleep stage and discover any abnormality during sleep.

While a vigorous weight loss and exercise program can reduce some of the soft tissue flabbiness and bulkiness that compromise the upper airway in the collapsible portion between the epiglottis and the nasopharynx, where snoring and obstructive sleep breathing occur, in practice, however, it is only the exceptional obstructive sleep apnea patient who can lose enough weight to make a significant difference. Moreover, many patients with sleep apnea are not physically active because of their chronic sleepiness and they often keep eating just to stay awake and make themselves feel better.

The airway can be kept patent with positive air pressure by the air-splint effect. Air can be injected through a nasal mask, such as from an air pump on the floor near the patient's bed. However, most mild apnea patients will not accept sleeping with a mask strapped on the face with airflow from a noisy air pump, because it is uncomfortable and keeps them awake.

Over the years, a variety of nasal dilator, nose braces, nasal strips, bandages, breathing equipment, jaw retainers, orthodontic inserts, tongue retainers, mechanisms, instruments and other devices have been suggested to improve the nasal airway and have met with varying degrees of success. Devices that require insertion into the nostrils have been tried, such as the Breathe EZ device. These devices are designed to open the nostrils and allow more air to enter the nose. Placement of devices and tubes inside the nose causes irritation, discomfort and increased resistance in most patients and, therefore, are not tolerated by many people. Various nasal strips have also been suggested. In one version of the Breathe Right nasal strip manufactured by CNS, Inc. of Minneapolis, Minn., adhesive strips are lined with two parallel plastic rods. When placed across the bridge of the nose, it adheres to the soft area above the flare of each nostril and provides an excessive pulling force to lift and open the nasal passages. In another version of the Breathe Right nasal strip, a flexible metal strip is attached to an adhesive band that is placed on the inside of the nose. The spring action of the metal strip pulls the sides of the nose outward. Breathe Right nasal strips and other prior nasal strips can be awkward, cumbersome, cause excessive forces on the nose, may cause pain when removed, and are only moderately effective.

It is, therefore, desirable to provide an improved nasal band to enhance breathing and reduce snoring, which overcomes most, if not all, of the preceding problems.

SUMMARY OF THE INVENTION

An improved nasal band is provided to enhance nasal breathing and reduce snoring. The inventive nasal band, which is also referred to as the Tip-Lift nasal band, enlarges the nasal openings, shortens the length of the nose, re-directs the flow of air from an upward angle of inclination to a more horizontal direction, and strengthens the sides of the nose to prevent nasal collapse. All these factors improve breathing by: reducing resistance of the air flowing through the nose, shortening the distance air has to travel though the nose, creating a more direct route for the air to flow and minimizing collapse of the sides of the nose so that the nasal chambers are not unduly restricted. Even people that breath adequately through their nose can breath even better by changing the position of the nasal tip with the inventive nasal band.

Advantageously, the inventive nasal band is comfortable, convenient, simple to use and effective. Desirably, the improved nasal band is light weight, unobtrusive, economical and user friendly. The inventive nasal band is also easier to wear and adheres better because there is less force pulling on the nasal skin.

In accordance with the invention, an improved adhesive nasal band is provided that when applied to the nasal tip and bridge of the nose, elevates the nasal tip. One end of the adhesive nasal band is applied to the nasal bridge and then to the forehead. The result is that the nasal tip is elevated by the inventive nasal band. The position of the nares or opening of the nose is changed by the special nasal band of the invention from a horizontal position to a more vertical position. This change in position of the nasal tip by the attractive nasal band achieves the following beneficial effects:

1. The direction of the air currents through the nose is changed. Instead of the air currents flowing in an upward direction when entering the nose, the direction of flow is changed to a more horizontal direct route to the back of the nose. This allows for less resistance of the air flowing through the nose resulting in easier breathing.

2. When the nasal tip is elevated, the length of the nose is shortened, therefore, there is less distance for the air to travel through the nose. This also reduces nasal resistance and makes breathing easier.

3. By elevating the nasal tip in the manner described with special nasal band of this invention, the sidewalls of the nose are thickened and shortened in an accordion effect. The thicker nasal side walls are stiffer and more resistant to inward collapse and compression during exercise or when rapid breathing occurs. The result is the thickened and stiffened nasal side walls help minimize nostril constriction when a negative pressure is created and decrease nasal sidewall collapse.

4. Elevating the nasal tip stretches and enlarges the nasal openings allowing more air to enter the nose.

The Tip-Lift nasal band can comprise an external nasal dilator which is worn lengthwise over the nose. The inventive nasal band improves the nasal airway by reducing nasal airflow resistance. This effect helps minimize mouth breathing therefore, decreases or eliminates snoring. Desirably, snoring severity and frequency improve in many patients when wearing the external nasal dilator comprising the Tip-Lift nasal band.

External nasal dilation with the inventive nasal band provides an increase in nasal valve airflow space. By increasing the anterior airway diameter, there is a decrease in airflow velocity, an increase in volume and a decrease in nasal pressure and resistance. Other concomitant benefits of the improved nasal band can include an increased threshold for airflow turbulence and fewer respiratory problems.

Advantageously, the nasal band comprises a flexible nasal dilator which extends above the tip of the nose. The flexible nasal dilator has a lower end which comprises a base for detachably engaging the tip of the nose and has an upper end which is positioned in registration with and is operatively connected to the base for detachably engaging a portion of the patient's face above the tip of the nose, such as on the patient's forehead, or between the patient's eyebrows, or the nasion between the patient's eye, or on the bridge of the nose. Desirably, the upper end of the nasal band cooperates with the lower end of the nasal band to enlarge the patient's nostrils, decrease nasal resistance, reduce the effective length of the nasal passageways, and move the nostrils to a more horizontal position to enhance breathing.

In the preferred form, the nasal band and dilator comprise a flexible band with sufficient strength to pull the tip of the nose upward without the use of wire, metal, springs, or rods. The flexible band can comprise: flexible tape, adhesive tape, laminated tape, flesh colored tape, porous tape, air permeable tape, breathable tape, medical tape, fabric, cloth, polyethylene, polypropylene, nylon, waxed fibers, composite fibers, flexible medical grade material, a flexible membrane, or combinations of the preceding.

In the preferred form, the nasal band has an enlarged top which comprises a forehead section that is removably secured and anchored to a patient's forehead. The nasal band can have a generally triangular base which can at least partially conform to the shape of the tip of the nose. The nasal band also has a bridge portion which extends along the bridge of the nose.

Preferably, the nasal band is positioned lengthwise and upwardly along the bridge of the nose. The nasal band can comprise a flexible strip with a maximum horizontal width and transverse span that is less than the overall width of the nose to avoid substantially covering the sides of the nose and contacting the patient's checks. The ends and middle of the nasal band have a self-sticking adhesive coating which securely attaches the nasal band to the patient's nose but which can readily be removed without pain or leaving ugly residue on the patient's nose.

A more detailed explanation of the invention is provided in the following description and appended claims taken in conjunction with the accompanying drawings.

DETAILED DESCRIPTION OF THE PREFERRED EMBODIMENT

A light weight nasal band 10 (FIGS. 1–4) provides a comfortable sleep band which improves the quality of sleep and makes breathing easier for many patients. The sleep band can also provide an effective anti-snoring device by improving the nasal airway, thus reducing mouth breathing.

Thickening the nasal sidewalls 11 and 12 prevents collapse, thus maintaining a good nasal airway. The nasal band further provides an attractive sports band which minimizes collapse of the nasal sidewalls during jogging, sports activities and other strenuous exercise so that athletes can continue to breathe through their nose rather than breathe through their open mouth.

The nasal band, which is also referred to as a Tip-Lift adhesive nasal band, can comprise a flexible composite elongated nasal dilator 14, which is positioned upwardly and lengthwise along the bridge 16 of a nose 17. The nasal band and dilator have an upper top membrane layer 18, an intermediate adhesive layer 20, and a lower bottom peelable layer 22.

Figure 1:
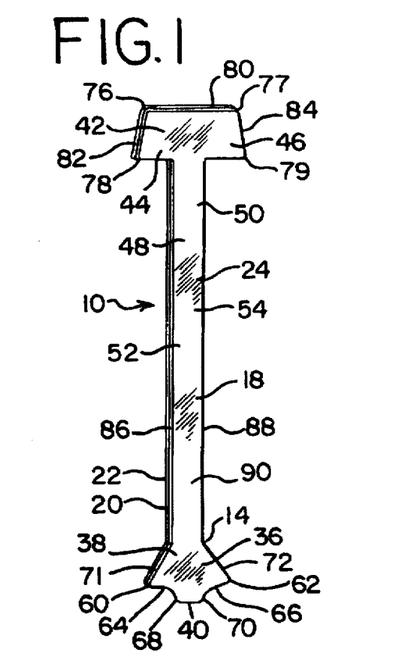
FIG. 1 is a front perspective view of a nasal band in accordance with principles of the present invention.
Figure 2:
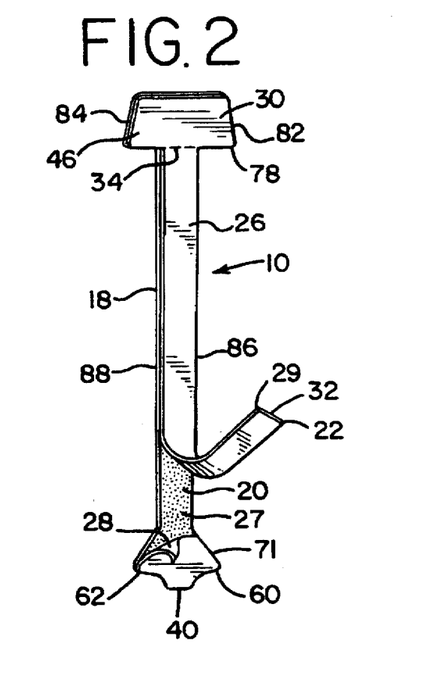
FIG. 2 is a back perspective view of the nasal band with portions peeled away for ease of understanding and clarity.
Figure 3:
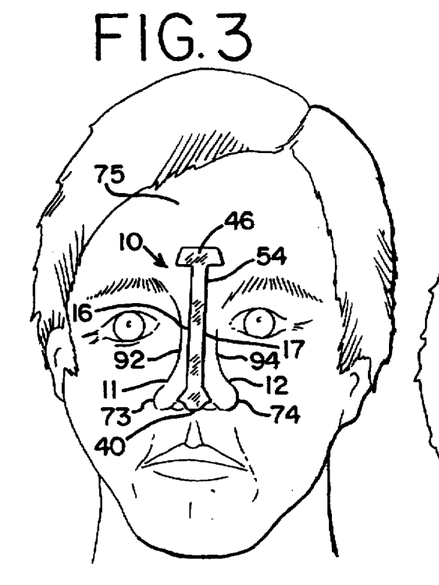
FIG. 3 is a front view of the nasal band on a patient's face.

The adhesive runs along the entire length of the band as does the peelable layer. This is designed so that the middle part adheres to the bridge of the nose. The upper membrane layer 18 of the nasal band and dilator can comprise flexible nasal tape with a front exterior surface 24 and a back surface 26 (FIG. 2). The flexible tape can comprise: adhesive tape, water impervious tape (waterproof tape), fluid impermeable tape, laminated tape, transparent tape, flesh colored tape, porous tape, air permeable tape, breathable tape, medical tape, or combinations of the preceding. The composition of the flexible tape can be made of one or more to the following: fabric, cloth, nylon, polyethylene, polypropylene, plastic, waxed fibers, composite fibers, or other flexible medical grade material. In preferred form, the tape comprises an adhesive transparent plastic tape.

The intermediate adhesive layer 20 (FIG. 2) of the nasal band and dilator comprise a self-sticking adhesive coating 27 or glue on a substantial portion of the back surface of the tape. The adhesive coating provides a tacky bondable surface which detachably secures the flexible tape to the nose and forehead. The adhesive keeps and maintains the nasal band on place on the nose and forehead.

The lower peelable layer 22 (FIG. 2) of the nasal band and dilator has at least one and preferably a plurality or set of removable peelable strips 28–30 of flexible paper or plastic which detachably cover the adhesive layer. The peelable strips can be separated by one or more cut lines 32 or perforations 34 and cooperate with the adhesive layer and tape to provide a peel and stick adhesive nasal band.

Figure 4:
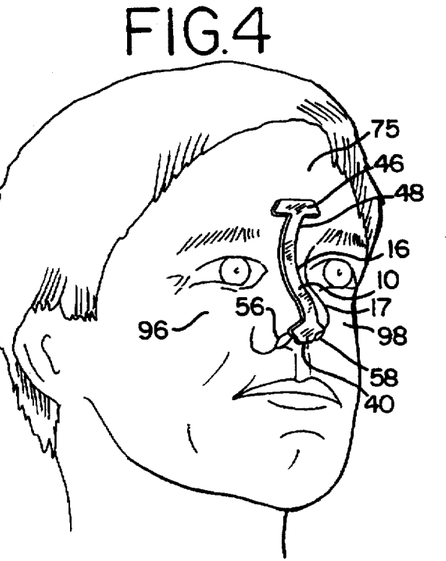
FIG. 4 is a side perspective view of the nasal band as applied to a patient's face.

The nasal band and dilator can have: a lower end 36 (FIG. 1) which provides a base 38 and comprises a flexible tip portion 40, an upper end 42 which provides an upper enlarged anchor section 44 and comprises a top forehead portion 46, and an elongated intermediate central connecting section 48 which provides a bight 50 and defines a narrow strip 52 that comprises an upright flexible, intermediate bridge portion 54. Advantageously, the forehead portion (upper end), bridge portion (intermediate narrow strip) and tip portion (lower end and base) cooperate with each other and have sufficient compressive strength to: (1) lift the tip of the nose as shown in FIG. 4, (2) enlarge the anterior nares 56 and 58 (FIG. 4) providing the inlet nasal openings of the nostrils, (3) shorten the effective length of the nasal passageways, (4) thicken the nasal sidewalls, (5) decrease nasal resistance, (6) substantially enhance breathing, (7) diminish nasal sidewall collapse, and (8) reduce snoring.

Preferably, the lower end 36 (FIG. 1) of the nasal band and dilator which provides a base 38 and comprises a flexible tip portion 40, has a shape and configuration which is substantially similar, complements and conforms to a substantial portion of the tip of the nose in order to detachably engage and securely attach to the tip of the nose. The tip portion (base) can have upwardly flared concave sections 60 and 62 which provide curved edges 64 and 66 and nostril openings 68 and 70 that are positioned adjacent to but do not block the anterior nares and nostrils of the nose. In the preferred embodiment, the base (tip portion) comprises a partially triangular base 38 with downwardly diverging, slanted straight sides 71 and 72 to detachably engage and securely attach to the alae nasi 73 and 74 (FIG. 3) comprising the outer flared cartilaginous walls of the nostrils. In some circumstances, it may be desirable to use a base (tip portion) with a different shape.

The upper end 42 (FIG. 1) of the nasal band and dilator, which provides an upper enlarged anchor section 44 and comprises a flexible forehead portion 46, is adapted and arranged to detachably engage and securely attach to the forehead 75 (FIGS. 3 and 4) at a location above the nose. The forehead section of the nasal band can be positioned in upright alignment with and disposed at an elevation generally vertically above the lower end comprising the base and tip portion of the nasal band.

In the illustrated embodiment, the forehead portion 46 (FIG. 1) of the nasal band and dilator is generally rectangular and wider than the intermediate bridge portion (narrow strip and bight). The rectangular forehead portion can have rounded corners 76–79, squared or perpendicular corners, can have a straight horizontal upper edge 80, and can have downwardly flared sides 82 and 84, such as downwardly diverging sides. The forehead portion of the nasal band can span a maximum width similar to the tip portion (base) of the nasal band. In some circumstances, it may be desirable that the forehead portion of the nasal band have a different shape, size, or be wider, narrower or the same widths as the intermediate bridge portion (narrow strip and bight) or the tip portion (base).

The intermediate central connecting section 48 (FIG. 1) of the nasal band and dilator that provides a bight 50 and defines a narrow strip 52 which comprises the intermediate bridge portion 54, extends between and integrally connects the tip portion (base) and the forehead portion. In the preferred embodiment, the bridge portion is rectangular with elongated parallel straight vertical sides 86 and 88. The bridge portion can extend substantially along the entire length of the nose. The bridge portion defines an upright crossbar 90 which detachably connects and securely attaches to the bridge of the nose. In the illustrative embodiment, the bridge portion of the nasal band spans a width which is narrower than the tip portion (base) and forehead portion of the nasal band. Preferably, the bridge portion of the nasal band is narrower than the nasal sidewalls, which comprise the nasal margin 92 and 94 (FIG. 3) that covers the upper nasal cartilage adjacent the nasal bridge and the alae nasi 73 and 74 that provides the outer flared cartilaginous walls of the nostrils, to avoid completely covering the nasal margins and contacting the patient's cheeks 96 and 98 (FIG. 4). In some circumstance, it may be desirable to use a different size or shaped bridge portion in the nasal band.

The nasal band can be packaged and stored generally flat so that the front exterior surfaces (top surface) of forehead portion, bridge portion and tip portion (base) of the flexible adhesive tape are positioned in coplanar alignment and registration with each other. Preferably, the nasal band is packaged, sealed and stored in a transparent wrapper, glassive package, paper envelope, sterile container, or other packaging which prevents contamination with dirt, debris and other substances.

The peelable strips 28–30 (FIG. 2) on the underside of the nasal band can be separated by cut lines 32 or perforations 34 between the tip portion (base) and bridge portion, as well as between the forehead portion and bridge portion, to facilitate removal of the peelable strips in order to apply the sticky adhesive tape of the composite nasal band to the nose, bridge and forehead. The nasal band preferably has 2–3 peelable strips which are shaped similar to the corresponding tip, bridge and forehead portions of the adhesive tape. The middle portion has to adhere to the nasal bridge to avoid a suspended bridge-type effect from the tip to the forehead. In some circumstances, it may be desirable that the nasal band has more or less peelable strips, or that parts of the bridge portion not be covered with an adhesive coating and peelable strips.

In order to use the nasal band, the nasal band is removed from its packaging by opening the packaging or container and withdrawing the nasal band. The peelable strips covering the adhesive coating can be peeled off and removed in a sequential manner before applying and contacting the adhesive tape of the nasal strip to the nose and forehead. The nasal band can be applied first to the nasal tip. While pulling upward on the adhesive band, the middle part providing the bridge portion of the nasal band is applied and adhered to the bridge of the nose. Continuing to pull up on the nasal band, the top part providing the forehead portion is applied to the forehead. Application of the nasal band in this matter allows the nasal openings to approach a more horizontal position when lying down or sleeping. When the nasal openings approach a more horizonal position, there is less resistance to air entering into the nose. Breathing is then made easier.

The method of applying the flexible nasal band comprising the special flexible adhesive strip, provides a particularly useful non-surgical procedure to improve breathing. Specifically, the lower adhesive end comprising the tip portion (base) of the flexible nasal band is detachably secured and applied to the tip of the nose. Desirably, the tip of the nose is lifted and pulled upwardly with the nasal band with sufficient force to enlarge the cross-sectional area of the anterior nares that provide the inlet nasal openings in order to increase nasal air flow and capacity. Advantageously, the requisite lifting and pulling is accomplished by the nasal band without the use of wire, spring, metal, or plastic rods as in prior nasal strips and devices because of the above-described special construction, shape and arrangement of the inventive nasal band.

The bridge portion (intermediate narrow strip) of the nasal band can be aligned, positioned, stretched, detachably secured and applied upwardly at an angle of inclination along the bridge of the patient's nose. Preferably, the bridge portion of the nasal band is applied, positioned and located upwardly (vertically) rather than horizontally, transversely and crosswise across the patient's nose so as to avoid contacting the cheeks of the patient (wearer).

Thereafter, the forehead portion (upper end) of the nasal band can be applied, detachably secured and removably bonded to a portion of the patient's forehead above the bridge of the nose and nasion between the patient's eye. Sometimes, it may be desirable to reverse the order and sequence of application steps, such as by applying the forehead portion to the forehead before the bridge portion is applied and removably secured (fastened) to the nasal bridge or before the tip portion (base) is applied and removably secured (fastened) to the nasal tip. Furthermore, in some circumstances it may be desirably to use a smaller or shorter nasal band, so that the upper end is secured to the nasal bridge or to the nasion between the eyes or to a portion between the eyebrows. The nasal band is flexible and when applied, conforms to the profile of the patient's nose (tip and bridge) and forehead.

Advantageously, when properly applied, the nasal band: (a) shortens the effective length of the nasal passageways while lifting the tip of the nose; (b) moves the nasal passageways to a more horizontal position while laying down, sleeping or standing upright; © decreases nasal resistance; (d) diminishes collapse of the nasal sidewalls comprising the alae nasi that provide the outer flared cartilaginous walls of the nostrils and the nasal margin which cover the upper nasal cartilage next to the nasal bridge, (e) thickens and compresses the nasal sidewalls; and (f) reduces snoring.

EXAMPLES 1–12

The inventive nasal band was tested on many patients. The nasal band had the preferred construction and shape as described above and as illustrated in the accompanying patent drawings. The nasal band was applied to the nasal tip, bridge, and forehead as described previously. The patients were of the age, sex, race and build indicated in the following chart.

|         | Patient | Age | Sex    | Race  | Build      |
|---------|---------|-----|--------|-------|------------|
| Example | 1       | 87  | Male   | White | Medium     |
| Example | 2       | 85  | Female | White | Overweight |
| Example | 3       | 13  | Male   | White | Medium     |
| Example | 4       | 16  | Female | White | Petite     |
| Example | 5       | 58  | Male   | White | Medium     |
| Example | 6       | 46  | Female | White | Medium     |
| Example | 7       | 49  | Female | White | Petite     |
| Example | 8       | 68  | Male   | White | Overweight |
| Example | 9       | 64  | Female | White | Petite     |
| Example | 10      | 28  | Female | White | Petite     |
| Example | 11      | 32  | Male   | White | Medium     |
| Example | 12      | 35  | Male   | Black | Medium     |

The tests provided surprising, unexpectedly good results. All patients report significant improvements in their nasal airways and breathing. Nasal resistance was reduced. No nasal sidewall collapse or snoring was observed. The nostril openings (anterior nares) were enlarged and stretched comfortably upwardly to shorten the effective length of the nasal passageways. The nostrils and nasal passageways were oriented, lifted and adjusted upwardly towards the forehead. Better nasal airflow and more oxygen intake occurred. Breathing was easier, better and more comfortable.

Among the many advantages of the inventive nasal band and improved method for enhanced breathing are:

1. Superb performance.
2. Outstanding consumer appeal for athletes, sleepers and snorers.
3. Better nasal airflow.
4. Easier breathing.
5. Reduced nasal resistance.
6. Helps prevent nasal sidewall collapse.
7. Decreased flapping of nasal sidewalls.
8. Less snoring.
9. Simple to use.
10. Excellent quality.
11. Comfortable.
12. Convenient.
13. Impressive.
14. Economical.
15. Portable.
16. Light weight.

17. Safe.
18. Desirable.
19. Efficient.
20. Effective.

Although embodiments of the invention have been shown and described, it is to be understood that various modifications and substitutions, as well as rearrangements of parts, components and process steps, can be made by those skilled in the art without departing from the novel spirit and scope of this invention.

What is claimed is:

1. A nasal band, comprising:
   a flexible nasal dilator for extending above a tip of a nose;
   said flexible nasal dilator having a lower end comprising a base for detachably engaging the tip of the nose and upper end positioned in registration with and operatively connected to said base for detachably engaging a portion of a patient's face above the tip of the nose; and
   said upper end cooperating with said base for lifting the tip of the nose to enlarge the patient's nostrils and decrease nasal resistance so as to enhance breathing.

2. A nasal band in accordance with claim 1 wherein:
   said dilator comprises a flexible band having sufficient strength to pull the tip of the nose upwardly in the absence of wire, metal, springs, and rods; and
   said portion of said patient's face is selected from the group consisting of a patient's forehead, a portion between the patient's eyebrows, a nasion between the patient's eye, and a bridge of the nose.

3. A nasal band in accordance with claim 1 having a bridge portion extending along a bridge of the nose, said bridge portion positioned between and connecting said lower end and said upper end.

4. A nasal band in accordance with claim 1 wherein said upper end of said flexible nasal dilator comprises a forehead section for removably securing and anchoring to the patient's forehead.

5. A nasal band in accordance with claim 1 wherein said upper end comprises an enlarged top.

6. A nasal band in accordance with claim 1 wherein said dilator is selected from the group consisting of: flexible tape, adhesive tape, transparent tape, laminated tape, flesh colored tape, porous tape, air permeable tape, breathable tape, water-resistant tape, medical tape, fabric, cloth, polyethylene, polypropylene, nylon, waxed fibers, composite fibers, flexible medical grade material, and a flexible membrane.

7. A nasal band in accordance with claim 1 wherein said base comprises a generally triangular base which at least partially conforms to the shape of said tip of the nose.

8. A nasal band in accordance with claim 1 wherein said dilator is positioned lengthwise and upwardly along a bridge of the nose and said dilator comprises a flexible strip having a maximum width less than the overall width of the nose to avoid substantially covering the sides of the nose and contacting the patient's cheeks.

9. A nasal band in accordance with claim 8 wherein said ends of said dilator have an adhesive coating.

10. A method for improved breathing, comprising the steps of:
    detachably securing a lower end of a flexible nasal band to the tip of a nose;
    lifting the tip of the nose with said nasal band with sufficient force to enlarge the cross-sectional area of the anterior nares providing increased inlet nasal openings for increased air flow and capacity without the use of wire, springs, metal or rods; and
    detachably securing an upper end of said nasal band above the tip of the nose.

11. A method in accordance with claim 10 including:
    avoiding positioning said nasal band transversely across the entire nose; and
    preventing the nasal band from contacting the wearer's cheeks by positioning and stretching the nasal band upwardly along the bridge of the nose.

12. A method in accordance with claim 10 including detachably securing the upper end of said nasal band to a forehead.

13. A method in accordance with claim 10 including detachably securing a middle portion of said nasal band to the nasal bridge.

14. A method in accordance with claim 12 wherein
    said nasal band comprise a flexible adhesive strip;
    said lifting includes pulling the tip of the nose upwardly with said flexible adhesive strip; and
    removably bonding said adhesive strip to the tip of the nose, nasal bridge, and the forehead.

15. A method in accordance with claim 10 including shortening the effective length of the nasal passageways with the nasal band while lifting the tip of the nose to decrease the pneumatic distance for the air to travel through the nose for improved breathing.

16. A method in accordance with claim 10 including moving the nasal passageways to a more horizontal position with said nasal band while lying down or sleeping for decreasing nasal resistance and reducing snoring.

17. A method in accordance with claim 10 including:
    reducing snoring with said nasal band by reducing nasal airflow resistance;
    improving the nasal airway;
    reducing airflow through the mouth;
    decreasing vibrations of the palate, tongue, and pharynx; and
    attenuating noise of snoring.

18. A nasal band, comprising:
    a flexible composite elongated nasal dilator for positioning upwardly and lengthwise along a bridge of a nose, said flexible composite elongated nasal dilator comprising
    an upper membrane layer comprising flexible nasal tape with a front exterior surface and back surface;
    an intermediate adhesive layer comprising a self-sticking adhesive coating disposed on a substantial portion of said back surface of said flexible tape for detachably securing said flexible tape to said nose;
    a lower peelable layer comprising at least one removable strip detachably covering said adhesive layer;
    said flexible composite elongated nasal dilator comprising
    a lower end providing a base comprising a flexible tip portion having a shape substantially similar, complementing and conforming to a substantial portion of the tip of the nose for detachably engaging and securing attaching to the tip of the said nose, said tip portion having upwardly flared concave sections providing curved edges for positioning adjacent to but not blocking anterior nares of the nose;
    an upper end providing an upper enlarged anchor section comprising a flexible forehead portion for detachably engaging and securing attaching to a forehead above the nose, said forehead section being substantially positioned in upright alignment with and above said tip portion;

an elongated intermediate central connecting section providing a bight comprising an upright flexible bridge portion extending between and integrally connecting said tip portion and said forehead portion, said bridge portion extending substantially along the entire length of a bridge of the nose, said bridge portion defining an upright crossbar for detachably connecting and securing attaching to the bridge of the nose, said bridge portion spanning a width narrower than said tip portion, forehead portion and nasal sidewalls comprising a margin covering upper nasal cartilage adjacent the bridge and alae nasi providing outer flared cartilaginous walls of the nostrils, to avoid completely covering the margin of the nasal sidewalls and contacting the cheeks; and said forehead portion, bridge portion and tip portion cooperating with each other and having sufficient compressive strength for lifting the tip of the nose to enlarge the anterior nares providing the inlet nasal openings of the nostrils, shortening the effective length of the nasal passageways, thickening the nasal sidewalls, and decreasing nasal air resistance, to substantially enhance breathing, diminish nasal sidewall collapse and reduce snoring.

19. A nasal band in accordance with claim 18 wherein:

said forehead portion comprises a substantially rectangular forehead portion; and said base comprises a partially triangular base with downwardly flared diverging sides for detachably engaging and securing attaching to the alae nasi comprising the outer flared cartilaginous walls of the nostrils.

20. A nasal band in accordance with claim 19 wherein:

said flexible tape is selected from the group consisting of: water impervious tape, fluid impermeable tape, adhesive tape, transparent tape, laminated tape, flesh colored tape, porous tape, air permeable tape, breathable tape, medical tape, and combinations thereof; and said flexible tape has a composition comprising at least one member of the group consisting of: fabric, cloth, nylon, polyethylene, polypropylene, plastic, waxed fibers, composite fibers, and flexible medical grade material.

* * * * *